US012745968B2

(12) United States Patent
Krug et al.

(10) Patent No.: US 12,745,968 B2
(45) Date of Patent: Sep. 29, 2026

(54) MEDICAL IMAGING SYSTEM AND METHOD FOR MOVING A COMPUTED TOMOGRAPHY GANTRY

(71) Applicant: Siemens Healthineers AG, Forchheim (DE)

(72) Inventors: Rita Krug, Fuerth (DE); Jan-Christoph Kiesel, Bayreuth (DE)

(73) Assignee: Siemens Healthineers AG, Forchheim (DE)

( * ) Notice: Subject to any disclaimer, the term of this patent is extended or adjusted under 35 U.S.C. 154(b) by 173 days.

(21) Appl. No.: 18/616,580

(22) Filed: Mar. 26, 2024

(65) Prior Publication Data

US 2024/0324973 A1 Oct. 3, 2024

(30) Foreign Application Priority Data

Mar. 30, 2023 (DE) ..................... 10 2023 202 908.1

(51) Int. Cl.
*A61B 6/00* (2024.01)
*A61B 6/03* (2006.01)

(52) U.S. Cl.
CPC ............ *A61B 6/035* (2013.01); *A61B 6/4405* (2013.01); *A61B 6/547* (2013.01)

(58) Field of Classification Search
CPC ........... A61B 5/70; A61B 6/04; A61B 6/0492; A61B 6/46; A61B 6/50; A61B 6/54
See application file for complete search history.

(56) References Cited

U.S. PATENT DOCUMENTS 6,212,251 B1 4/2001 Tomura et al.
2003/0095635 A1 * 5/2003 Moritake ............... A61B 6/035 378/198
2023/0202283 A1 6/2023 Braeuer et al.

FOREIGN PATENT DOCUMENTS

DE 102021215076 A1 6/2023
JP 2015058045 A 3/2015

* cited by examiner

*Primary Examiner* — Dani Fox
(74) *Attorney, Agent, or Firm* — Harness, Dickey & Pierce, P.L.C.

(57) ABSTRACT

One or more example embodiments of the present invention relates to a medical imaging system comprising a computed tomography gantry; a carriage; and a rail system, wherein the computed tomography gantry is movably mounted via the carriage and the rail system such that the computed tomography gantry is translationally movable along the rail system, and the carriage and the rail system are configured to transmit a driving force for the translational movement of the computed tomography gantry in a non-positive locking manner from the carriage to the rail system.

17 Claims, 2 Drawing Sheets

MEDICAL IMAGING SYSTEM AND METHOD FOR MOVING A COMPUTED TOMOGRAPHY GANTRY

CROSS-REFERENCE TO RELATED APPLICATION(S)

The present application claims priority under 35 U.S.C. § 119 to German Patent Application No. 10 2023 202 908.1, filed Mar. 30, 2023, the entire contents of which is incorporated herein by reference.

FIELD

One or more example embodiments of the present invention relates to a medical imaging system. One or more example embodiments of the present invention further relates to a method for moving a computed tomography gantry.

RELATED ART

In computed tomography (CT), during a scan of an object to be examined, the longitudinal position of a computed tomography gantry relative to the object to be examined is changed, for example, based on a continuous translational movement, and is continuously detected for the imaging system. The accuracy of the translational movement and the position detection is important for the image quality. For example, an accuracy in the sub-millimeter range can be required for sufficient image quality. The movement of the computed tomography gantry relative to the object to be examined can be driven, for example, in a positive-locking manner, in particular via a gearwheel and a rack, wherein the rack is firmly anchored relative to the base surface.

A positive-locking drive, for example a rack and pinion drive or a belt drive, requires an engagement region in which the positive locking takes place and which accordingly has a significantly structured surface that is difficult to clean, forms a tripping point and/or is mechanically sensitive. For hygienic reasons, a protective cover of the intervention area must be tight against liquids in the clinical environment. In addition, it should be robust and resilient and allow the passage of patient beds and instrument tables.

SUMMARY

This is typically associated with high costs, a high maintenance effort and a hygiene risk. In addition, a raising of the floor installations and/or a relatively complex installation is often required for the integration of such a cover.

One or more example embodiments of the present invention enables a movement of a computed tomography gantry, which is improved with regard to the installation, maintenance of and ability to clean the components involved.

Each subject matter of an independent claim solves this object. Further advantageous aspects of the invention are taken into consideration in the dependent claims. Irrespective of the grammatical gender of a certain term, persons with a male, female or other gender identity are included.

BRIEF DESCRIPTION OF THE DRAWINGS

The invention is explained below with the aid of exemplary embodiments with reference to the attached figures. The representation in the figures is schematic, greatly simplified and not necessarily to scale.

DETAILED DESCRIPTION

Figure 1:
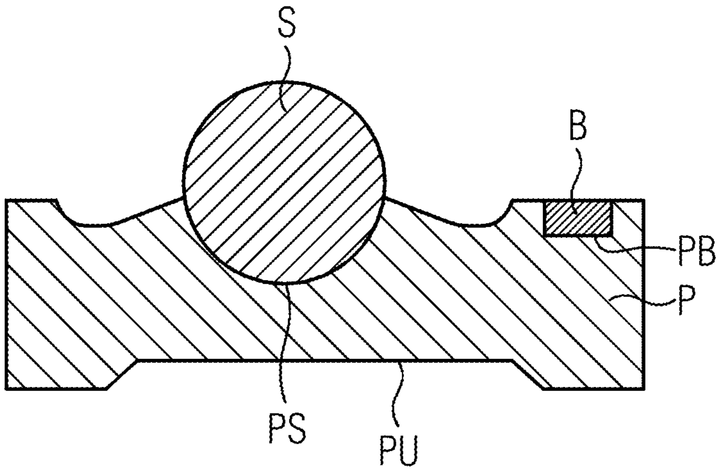
FIG. 1 shows a supporting profile, a rail and a measurement track in a first view.

One or more example embodiments of the present invention relates to a medical imaging system having a computed tomography gantry, a carriage and a rail system,

- wherein the computed tomography gantry is movably mounted via the carriage and the rail system in such a manner that a translational movement of the computed tomography gantry can be performed along the rail system,
- wherein the carriage and the rail system are configured so as to transmit a driving force for the translational movement of the computed tomography gantry in a non-positive locking manner from the carriage to the rail system, in particular by friction.

In particular, it can be provided that the rail system rests relative to a base surface and/or is firmly anchored relative to the base surface. In particular, it can be provided that an object to be examined rests relative to the rail system and/or relative to the base surface. The rail system can in particular form a linear guide for the carriage.

For example, the medical imaging system can have an examination table for mounting the object to be examined. In particular, the examination table can rest relative to the rail system and/or relative to the base surface and/or be firmly anchored relative to the rail system and/or relative to the base surface. The object to be examined can, for example, be a person to be examined, in particular a patient, and/or can be mounted on the examination table, in particular can be mounted in a resting position relative to the examination table.

The translational movement can in particular take place relative to the rail system, relative to the base surface, relative to the examination table and/or relative to the object to be examined. The translational movement can in particular be essentially horizontal. The base surface can in particular be essentially horizontal. The base surface can in particular be a floor of an examination room.

The computed tomography gantry can, for example, have a supporting frame and a rotor that is rotatably mounted relative to the supporting frame, wherein the radiation source and the radiation detector are arranged on the rotor. Optionally, the computed tomography gantry can have a tilting frame that is mounted so as to be tiltable relative to the supporting frame, wherein the rotor is arranged on the tilting frame. The radiation source and the radiation detector can cooperate for recording a projection data set of the object to be examined. The computed tomography gantry can, for example, have an opening. In particular, the rail system, the examination table, and the opening can be arranged relative to one another in such a manner that, due to the translational movement of the computed tomography gantry, the examination table is introduced into the opening, in particular is introduced into the opening together with the object to be examined, which is mounted on the examination table.

One embodiment provides that a set of wheel-rail roller contacts is formed between the carriage and the rail system, wherein the carriage and the rail system are configured so as to transmit the driving force for the translational movement of the computed tomography gantry via the set of wheel-rail roller contacts in a non-positive locking manner from the carriage to the rail system.

One embodiment provides that the set of wheel-rail roller contacts receives the entire weight force of the carriage and the computed tomography gantry, wherein each wheel-rail roller contact, which is included in the set of wheel-rail roller contacts and receives at least a part of the entire weight force of the carriage and the computed tomography gantry, transmits at least a part of the driving force for the translational movement of the computed tomography gantry in a non-positive locking manner, in particular by friction.

In particular, it can be provided that the at least one part of the entire weight force of the carriage and the computed tomography gantry is not insignificant, for example is greater than one tenth of the entire weight force of the carriage and the computed tomography gantry. In particular, it can be provided that the at least one part of the driving force for the translational movement of the computed tomography gantry is not insignificant, for example is greater than one tenth of the driving force for the translational movement of the computed tomography gantry.

In particular, it can be ruled out for the medical imaging system that there is a wheel-rail roller contact, which, although it receives a part of the entire weight force of the carriage and the computed tomography gantry, does not transmit a part of the driving force for the translational movement of the computed tomography gantry.

Compared to a friction wheel drive, the solution in accordance with one or more example embodiments of the present invention renders it possible in principle to transmit a higher driving force. The friction force that is available for the drive depends on the friction coefficient and the normal force with which the friction wheel is loaded. In particular, if the wheel is driven directly and the friction of the wheel-rail roller contacts is used, the entire weight force of the carriage and the computed tomography gantry can be used as a normal force. In the case of a friction wheel, there is a distribution of the weight force between the rail wheels and the friction wheel, so that only a part of the weight force is available as a normal force.

One embodiment provides that the rail system has a set of rails, wherein the carriage has a set of wheels, wherein the set of wheels is arranged so as to roll on the set of rails.

In particular, it can be provided that the set of rails and the set of wheels form the set of wheel-rail roller contacts. In particular, it can be provided that each rail of the set of rails is a round rail and/or that each wheel of the set of wheels is designed as a concave roller and/or for rolling on a round rail. The rails and/or the wheels can be made of steel, for example.

In particular, the round rails can be integrated into the floor without a cover and without drive elements, and in this case render it possible for patient beds and instrument tables to pass over. The driving force for the translational movement of the computed tomography gantry can be transmitted from the carriage to the rail system, for example, based on a non-positive locking connection, in particular a frictional connection, between the wheels of the set of wheels and the rails of the set of rails.

One embodiment provides that for each wheel of the set of wheels the carriage has a wheel direct drive, which interacts with this wheel and contributes proportionally to the driving force for the translational movement of the computed tomography gantry.

In particular, it can be provided that for each wheel of the set of wheels the wheel direct drive, which interacts with this wheel, drives this wheel directly and consequently contributes proportionally to the driving force for the translational movement of the computed tomography gantry. In particular, it can be provided that the driving force for the translational movement of the computed tomography gantry is generated by the wheel direct drives of the wheels of the set of wheels together. The direct wheel drive can have, for example, an electric motor, in particular an electric wheel hub motor.

One embodiment provides that the medical imaging system further has a position measuring system and that the position measuring system is configured so as to generate position information, wherein the position information relates to a position of the computed tomography gantry along the rail system.

The position of the computed tomography gantry along the rail system can be defined in particular relative to a reference point that rests relative to the base surface and/or relative to the rail system, in particular during the translational movement of the computed tomography gantry relative to the base surface and/or relative to the rail system. In particular, it can be provided that the position of the computed tomography gantry along the rail system is measured continuously, in particular at a sufficiently high sampling rate, during the translational movement of the computed tomography gantry, in particular is measured in such a manner that the position information for each projection data set, which was recorded via the computed tomography gantry, of an object to be examined during the translational movement of the computed tomography gantry comprises a position of the computed tomography gantry at which this projection data set was recorded.

One embodiment provides that the position measuring system is configured so as to generate the position information based on a measurement, in particular based on a contactless measurement, of the position of the computed tomography gantry along the rail system.

The contactless measurement can be performed, for example, optically, magnetically, magnetostrictively, inductively and/or capacitively and/or can be based on a transit time measurement. The combination of a non-positive drive force transmission between the wheel and the rail on the one hand and the contactless position measurement on the other hand enables precise positioning and position detection of the carriage with a minimum engagement surface, wherein both in the drive and in the position measurement it is possible to omit a positive-locking connection. This improves the ability to clean and reduces wear.

The measurement of the position of the computed tomography gantry along the rail system can be performed in particular absolutely, for example via an absolute value encoder, or incrementally, for example via an incremental encoder.

One embodiment provides that the position measuring system has a measurement track and a position sensor, wherein the measurement track rests relative to the rail system and extends along the rail system, wherein the position sensor is connected to the carriage in such a manner that it follows the translational movement of the computed tomography gantry and interacts with the measurement track during the translational movement of the computed tomography gantry, in particular in order to perform the measurement, in particular the contactless measurement, of the position of the computed tomography gantry along the rail system.

The measurement track can be for example a code track. The position sensor can in particular be configured so as to scan the code track. The measurement track can be, for example, a magnetic tape. The magnetic tape can in particular be magnetized at regular intervals. The measurement track can be, for example, a measuring tape, in particular a stainless steel measuring tape, and/or be firmly anchored relative to the base surface.

One embodiment provides that the medical imaging system also has a supporting profile, and that the supporting profile has a measurement track groove for receiving, in particular for receiving in a positive-locking manner, the measurement track, and the measurement track is received in the measurement track groove, in particular is received in a positive-locking manner, wherein the supporting profile has a rail groove for receiving a rail of the rail system in a positive-locking manner, and the rail of the rail system is received in the rail groove in a positive-locking manner.

In particular, it can be provided that the supporting profile extends along the rail system and/or that the supporting profile is firmly anchored relative to the base surface. In particular, the measurement track groove and the rail groove can be arranged essentially parallel to one another. In particular, the measurement track can be adhesively bonded to the supporting profile.

One embodiment provides that the medical imaging system further has a data processing unit and that the data processing unit is configured so as to calculate a drive signal based on the position information, wherein the carriage has a travel drive, wherein the travel drive is configured so as to generate the driving force for the translational movement of the computed tomography gantry in dependence upon the drive signal.

In particular, it can be provided that the wheel direct drives of the wheels of the set of wheels together form the travel drive.

One or more example embodiments of the present invention further relates to a method for moving a computed tomography gantry, wherein the computed tomography gantry is movably mounted via a carriage and a rail system in such a manner that a translational movement of the computed tomography gantry can be performed along the rail system, the method comprising:

performing the translational movement of the computed tomography gantry along the rail system, wherein a driving force for the translational movement of the computed tomography gantry is transmitted in a non-positive locking manner from the carriage to the rail system, in particular is transmitted by friction.

One embodiment provides that a set of wheel-rail roller contacts is formed between the carriage and the rail system, wherein the driving force for the translational movement of the computed tomography gantry is transmitted via the set of wheel-rail roller contacts in a non-positive locking manner to the rail system.

One embodiment provides that the entire weight force of the carriage and the computed tomography gantry is received by the set of wheel-rail roller contacts, wherein at least a part of the driving force for the translational movement of the computed tomography gantry is transmitted in a non-positive locking manner, in particular is transmitted by friction, by each wheel-rail roller contact, which is included in the set of wheel-rail roller contacts and receives at least a part of the entire weight force of the carriage and the computed tomography gantry.

One embodiment provides that the method further comprises:

generating position information via a position measuring system while performing the translational movement of the computed tomography gantry along the rail system, wherein the position information relates to a position of the computed tomography gantry along the rail system, providing the position information.

The position information can be provided, for example, by transmitting a signal that carries the position information and/or by writing the position information to a computer-readable storage medium and/or by displaying the position information on a screen. The position information can be used, for example, in an image reconstruction from projection data sets that were recorded via the computed tomography gantry of an object to be examined during the translational movement of the computed tomography gantry.

One embodiment provides that a drive signal is calculated based on the position information via a data processing unit, wherein the driving force for the translational movement of the computed tomography gantry is generated via a travel drive of the carriage in dependence upon the drive signal, in particular in order to thereby control and/or regulate the translational movement of the computed tomography gantry.

It is possible due to the non-positive-locking drive to omit a positive-locking drive, for example in the form of a rack and pinion drive. As a result, further components can be saved and the maintenance outlay can be reduced. This results in savings in product costs and product life cycle costs with improved technical reliability.

A further advantage is the significantly smaller installation space required in the floor, in particular the height. Compared to a rack and pinion drive, in the solution in accordance with one or more example embodiments of the present invention the required installation space in the floor can be reduced, for example, from approximately 120 mm to approximately 60 mm, whereby the installation becomes less complex. Compared to a friction wheel drive, the installation of a running surface for the friction wheel can be omitted.

A medical system having a supporting structure, a carriage and a rail system is further hereby disclosed, wherein the supporting structure is movably mounted via the carriage and the rail system in such a manner that a translational movement of the supporting structure can be performed along the rail system, wherein the carriage and the rail system are configured so as to transmit a driving force for the translational movement of the supporting structure in a non-positive locking manner from the carriage to the rail system.

The medical system having the supporting structure can be designed, for example, in analogy to one of the aspects that are described for the medical imaging system having the computed tomography gantry. The medical system can be, for example, an X-ray imaging system, in particular having a C-arm as a supporting structure, a magnetic resonance imaging system, in particular having a supporting structure that holds the body coil, or a radiation therapy device, in particular having a supporting structure that holds the radiation source.

Within the scope of the invention, it is possible for features that are described in relation to different embodiments of the invention and/or different claim categories (method, use, apparatus, system, arrangement etc.) to be combined to form further embodiments of the invention. For example, a claim that relates to an apparatus can also be developed using features that are described or claimed in relation to a method and vice versa. Functional features of a method in this case can be performed by accordingly designed objective components.

The use of the indefinite article "a" or "an" does not rule out that the relevant feature can also be provided multiple times. The term "based on" can be understood in the context of the present application in particular in the sense of the term "using". In particular, a wording according to which a first feature is calculated based on a second feature (alternatively: determined, generated, etc.) does not exclude that the first feature can further be calculated based on a third feature (alternatively: determined, generated, etc.).

Figure 2:
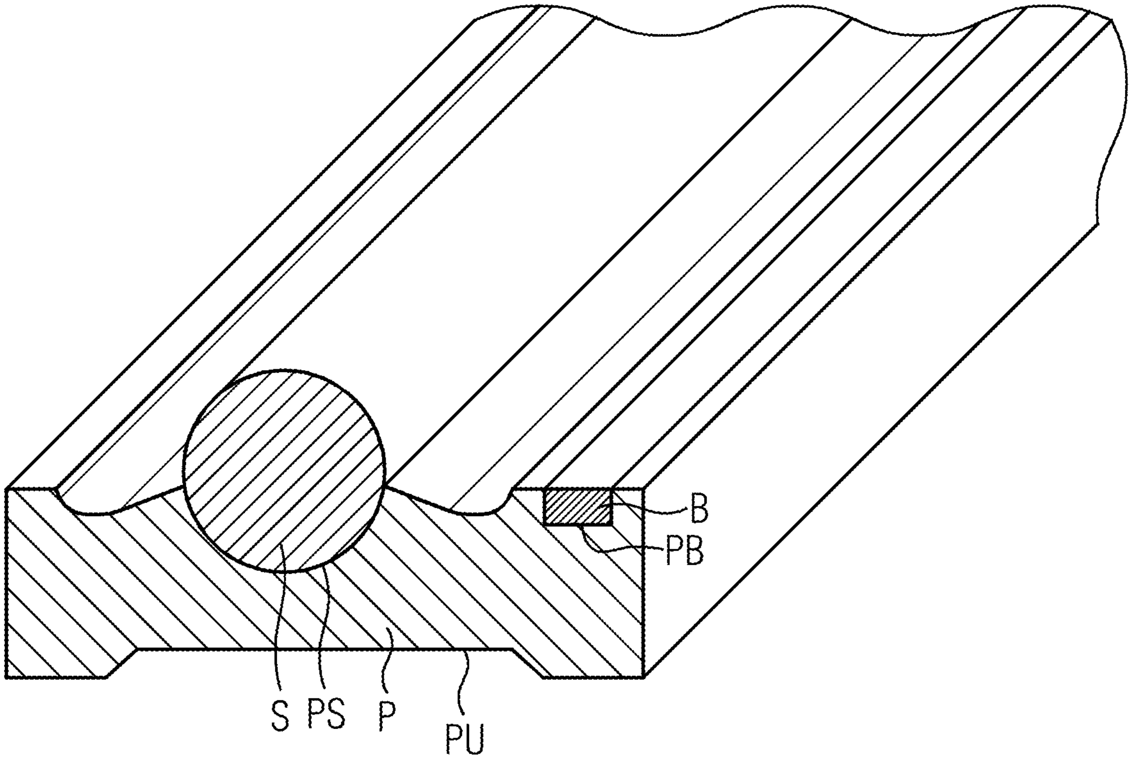
FIG. 2 shows the supporting profile, the rail and the measurement track in a second view.

FIG. 1 illustrates the supporting profile P, the rail S, and the measurement track B in a first view, wherein the supporting profile P has a measurement track groove PB for receiving the measurement track B in a positive-locking manner, and the measurement track B is received in the measurement track groove PB in a positive-locking manner, wherein the supporting profile P has a rail groove PS for receiving a rail S of the rail system L in a positive-locking manner, and the rail S of the rail system L is received in the rail groove PS in a positive-locking manner. The supporting profile P has the anchoring structure PU for positive-locking anchoring in a corresponding recess of the base surface U. FIG. 2 illustrates the supporting profile P, the rail S and the measurement track B in a second view.

Figure 3:
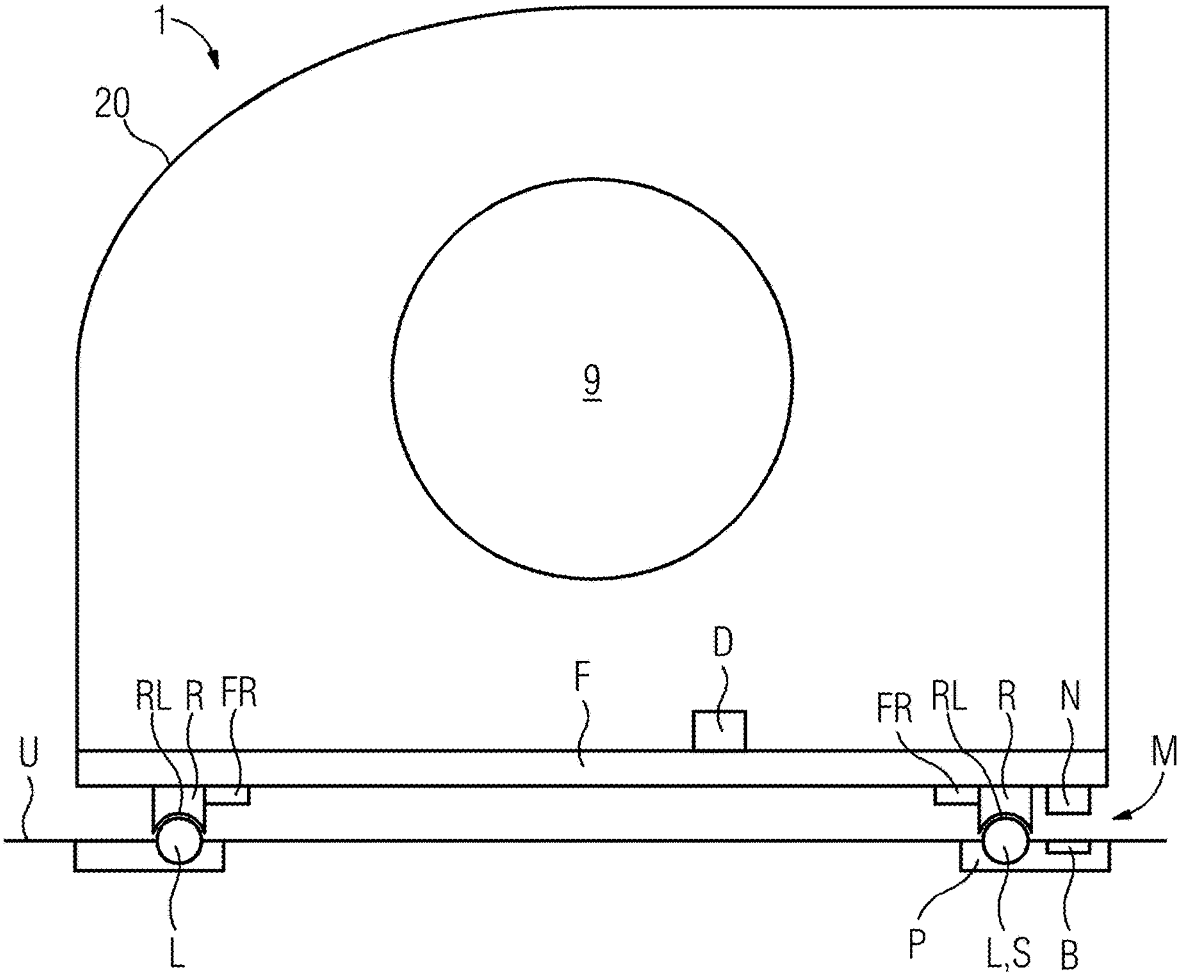
FIG. 3 shows a medical imaging system having a computed tomography gantry, a carriage and a rail system.

FIG. 3 illustrates the medical imaging system 1, having the computed tomography gantry 20, the carriage F and the rail system L, wherein the computed tomography gantry 20 is movably mounted via the carriage F and the rail system L in such a manner that a translational movement of the computed tomography gantry 20 can be performed along the rail system L, wherein the carriage F and the rail system L are configured so as to transmit a driving force for the translational movement of the computed tomography gantry 20 in a non-positive locking manner from the carriage F to the rail system L.

A set of wheel-rail roller contacts is formed between the carriage F and the rail system L, wherein the carriage F and the rail system L are configured so as to transmit the driving force for the translational movement of the computed tomography gantry 20 via the set of wheel-rail roller contacts RL in a non-positive locking manner from the carriage F to the rail system L. The set of wheel-rail roller contacts RL receives the entire weight force of the carriage F and the computed tomography gantry 20, wherein each wheel-rail roller contact, which is included in the set of wheel-rail roller contacts RL and receives at least a part of the entire weight force of the carriage F and the computed tomography gantry 20, transmits at least a part of the driving force for the translational movement of the computed tomography gantry 20 in a non-positive locking manner. The rail system L has a set of rails, wherein the carriage F has a set of wheels R, wherein the set of wheels R is arranged so as to roll on the set of rails. For each wheel of the set of wheels R, the carriage F has a wheel direct drive, which interacts with this wheel and contributes proportionally to the driving force for the translational movement of the computed tomography gantry 20.

The medical imaging system 1 further has the position measuring system M, wherein the position measuring system M is configured so as to generate S2 position information, wherein the position information relates to a position of the computed tomography gantry 20 along the rail system L. The position measuring system M is configured so as to generate S2 the position information based on a contactless measurement of the position of the computed tomography gantry 20 along the rail system L. The position measuring system M has the measurement track B and the position sensor N, wherein the measurement track B rests relative to the rail system L and extends along the rail system L, wherein the position sensor N is connected to the carriage F in such a manner that the position sensor follows the translational movement of the computed tomography gantry 20 and interacts with the measurement track B during the translational movement of the computed tomography gantry 20. For example, a corresponding position measuring system, in particular having a measurement track and position sensor, can also be provided in the region of the other rail of the rail system L (in the left-hand part of FIG. 3).

The medical imaging system 1 further has a data processing unit D, wherein the data processing unit D is configured so as to calculate a drive signal based on the position information, wherein the carriage F has a travel drive FR, wherein the travel drive FR is configured so as to generate the driving force for the translational movement of the computed tomography gantry 20 in dependence upon the drive signal.

The computed tomography gantry 20 has the opening 9. Due to the translational movement of the computed tomography gantry 20, an examination table can be introduced into the opening 9, in particular can be introduced into the opening 9 together with an object to be examined, which is mounted on the examination table.

Figure 4:
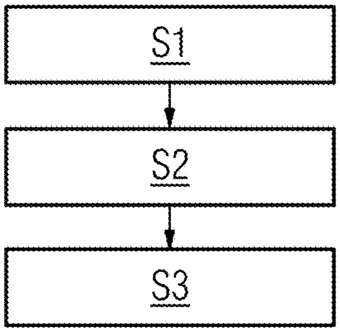
FIG. 4 shows a flowchart of a method for moving a computed tomography gantry.

FIG. 4 illustrates a flowchart of a method for moving a computed tomography gantry 20, wherein the computed tomography gantry 20 is movably mounted via a carriage F and a rail system L in such a manner that a translational movement of the computed tomography gantry 20 can be performed along the rail system L, the method comprising:

- performing S1 the translational movement of the computed tomography gantry 20 along the rail system L, wherein a driving force for the translational movement of the computed tomography gantry 20 is transmitted in a non-positive locking manner from the carriage F to the rail system L,
- generating S2 position information via a position measuring system M while performing S1 the translational movement of the computed tomography gantry 20 along the rail system L, wherein the position information relates to a position of the computed tomography gantry 20 along the rail system L,
- providing S3 the position information.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although the disclosure has been shown and described with respect to certain preferred embodiments, equivalents and modifications will occur to others skilled in the art upon the reading and understanding of the specification. The present disclosure includes all such equivalents and modifications and is limited only by the scope of the appended claims.

The invention claimed is:

1. A medical imaging system comprising:

a computed tomography gantry;

a rail system, the rail system including a set of rails; and a carriage, the carriage including a set of wheels configured to roll on the set of rails, wherein the computed tomography gantry is movably mounted via the carriage and the rail system such that the computed tomography gantry is translationally movable along the rail system, the carriage and the rail system are configured to transmit a driving force for the translational movement of the computed tomography gantry in a non-positive locking manner from the carriage to the rail system, and the carriage has a set of wheel direct drives, each respective wheel direct drive among the set of wheel direct drives interacts with a corresponding wheel among the set of wheels and contributes proportionally to the driving force.

2. The medical imaging system as claimed in claim 1, wherein a set of wheel-rail roller contacts is between the carriage and the rail system; and the carriage and the rail system are configured to transmit the driving force via the set of wheel-rail roller contacts in a non-positive locking manner from the carriage to the rail system.

3. The medical imaging system of claim 2, wherein the set of wheel-rail roller contacts receives an entire weight force of the carriage and the computed tomography gantry; and each wheel-rail roller contact among the set of wheel-rail roller contacts is configured to, receives at least a part of the entire weight force of the carriage and the computed tomography gantry, and transmits at least a part of the driving force in a non-positive locking manner.

4. The medical imaging system of claim 1, further comprising:

a position measuring system configured to generate position information, the position information relating to a position of the computed tomography gantry along the rail system.

5. The medical imaging system of claim 4, wherein the position measuring system is configured to generate the position information based on a contactless measurement of the position.

6. The medical imaging system of claim 4, wherein the position measuring system has a measurement track and a position sensor;

the measurement track rests relative to the rail system and extends along the rail system; and the position sensor is connected to the carriage such that the position sensor follows the translational movement of the computed tomography gantry and interacts with the measurement track during the translational movement of the computed tomography gantry.

7. The medical imaging system of claim 6, further comprising:

a supporting profile, the supporting profile including, a measurement track groove configured to receive the measurement track, and a rail groove configured to receive a rail of the rail system in a positive-locking manner.

8. A method for moving a computed tomography gantry, the computed tomography gantry being movably mounted via a carriage including a set of wheels and a rail system including a set of rails, the set of wheels being configured to roll on the set of rails, the carriage having a set of wheel direct drives, each respective wheel direct drive among the set of wheel direct drives interacting with a corresponding wheel among the set of wheels and contributing proportionally to a driving force for a translational movement of the computed tomography gantry, the method comprising:

performing the translational movement of the computed tomography gantry along the rail system, the driving force being transmitted in a non-positive locking manner from the carriage to the rail system.

9. The method of claim 8, wherein, a set of wheel-rail roller contacts is between the carriage and the rail system; and the driving force for the translational movement of the computed tomography gantry is transmitted via the set of wheel-rail roller contacts in a non-positive locking manner from the carriage to the rail system.

10. The method of claim 9, wherein, an entire weight force of the carriage and the computed tomography gantry is received by the set of wheel-rail roller contacts; and at least a part of the driving force for the translational movement of the computed tomography gantry is transmitted in a non-positive locking manner by each wheel-rail roller contact, which is included in the set of wheel-rail roller contacts and receives at least a part of the entire weight force of the carriage and the computed tomography gantry.

11. The method of claim 8, further comprising:

generating position information via a position measuring system while performing the translational movement of the computed tomography gantry along the rail system, wherein the position information relates to a position of the computed tomography gantry along the rail system; and providing the position information.

12. The method of claim 11, wherein a drive signal is calculated based on the position information via a data processing unit; and the driving force for the translational movement of the computed tomography gantry is generated via a travel drive of the carriage in dependence upon the drive signal.

13. The medical imaging system of claim 4, further comprising:

a data processing unit configured to calculate a drive signal based on the position information, and the carriage has a travel drive, wherein the travel drive is configured to generate the driving force for the translational movement of the computed tomography gantry based on the drive signal.

14. The medical imaging system of claim 5, further comprising:

a data processing unit configured to calculate a drive signal based on the position information, and the carriage has a travel drive, wherein the travel drive is configured to generate the driving force for the translational movement of the computed tomography gantry based on the drive signal.

15. The medical imaging system of claim 6, further comprising:

a data processing unit configured to calculate a drive signal based on the position information, and the carriage has a travel drive, wherein the travel drive is configured to generate the driving force for the translational movement of the computed tomography gantry based on the drive signal.

16. A medical imaging system comprising:

a computed tomography gantry;

a carriage;

a rail system, wherein the computed tomography gantry is movably mounted via the carriage and the rail system such that the computed tomography gantry is translationally movable along the rail system, and the carriage and the rail system are configured to transmit a driving force for the translational movement of the computed tomography gantry in a non-positive locking manner from the carriage to the rail system;

a position measuring system configured to generate position information, wherein, the position information relates to a position of the computed tomography gantry along the rail system, the position measuring system includes a measurement track and a position sensor, the measurement track rests relative to the rail system and extends along the rail system, and the position sensor is connected to the carriage such that the position sensor follows the translational movement of the computed tomography gantry and interacts with the measurement track during the translational movement of the computed tomography gantry; and a supporting profile, the supporting profile including, a measurement track groove configured to receive the measurement track, and a rail groove configured to receive a rail of the rail system in a positive-locking manner.

17. The medical imaging system of claim 16, further comprising:

a data processing unit configured to calculate a drive signal based on the position information, and the carriage has a travel drive, wherein the travel drive is configured to generate the driving force for the translational movement of the computed tomography gantry based on the drive signal.

* * * * *